United States Patent
Zangen et al.

(10) Patent No.: US 9,808,642 B2
(45) Date of Patent: Nov. 7, 2017

(54) CIRCULAR COILS FOR DEEP TRANSCRANIAL MAGNETIC STIMULATION

(71) Applicant: BRAINSWAY, LTD., Jerusalem (IL)

(72) Inventors: Abraham Zangen, Jerusalem (IL); Yiftach Roth, Rechelim (IL)

(73) Assignee: BRAINSWAY, LTD., Jerusalem (IL)

( * ) Notice: Subject to any disclaimer, the term of this patent is extended or adjusted under 35 U.S.C. 154(b) by 0 days.

(21) Appl. No.: 15/011,747

(22) Filed: Feb. 1, 2016

(65) Prior Publication Data

US 2016/0206895 A1   Jul. 21, 2016

Related U.S. Application Data

(63) Continuation-in-part of application No. 13/772,449, filed on Feb. 21, 2013, now Pat. No. 9,248,308.

(51) Int. Cl.
*A61N 2/02* (2006.01)
*A61N 2/00* (2006.01)

(52) U.S. Cl.
CPC ............... *A61N 2/02* (2013.01); *A61N 2/006* (2013.01)

(58) Field of Classification Search
CPC . A61N 2/02; A61N 2/006; A61N 1/40; A61N 1/37229; A61B 5/055; A61B 5/06; G01R 33/3415; H01F 7/202; G06F 17/5009; G06F 2271/09
USPC ............. 128/897–899; 600/9–15, 417; 607/2
See application file for complete search history.

(56) References Cited

U.S. PATENT DOCUMENTS

| | | | | |
|---|---|---|---|---|
| 2006/0094924 A1* | 5/2006 | Riehl | ..................... | A61N 2/006 600/9 |
| 2006/0287566 A1* | 12/2006 | Zangen | .................... | A61N 2/02 600/15 |
| 2008/0312706 A1* | 12/2008 | Zangen | ................... | A61N 2/006 607/2 |
| 2011/0184223 A1* | 7/2011 | Peterchev | .............. | A61N 2/006 600/14 |
| 2011/0273251 A1* | 11/2011 | Mishelevich | .......... | A61N 2/006 335/299 |
| 2011/0288364 A1* | 11/2011 | Zangen | .................... | A61N 2/02 600/13 |

* cited by examiner

*Primary Examiner* — Navin Natnithithadha
*Assistant Examiner* — Sunita Reddy
(74) *Attorney, Agent, or Firm* — Daniel J. Swirsky; Ricki L. Simon; AlphaPatent Associates Ltd.

(57) ABSTRACT

A transcranial magnetic stimulation coil which is location-specific for frontal lobe regions, occipital lobe regions, parietal lobe regions, right temporal regions and left temporal regions is designed with multiple spaced apart stimulating elements having current flow in a substantially circular direction, and multiple return elements having current flow in substantially the same circular direction.

17 Claims, 17 Drawing Sheets

CIRCULAR COILS FOR DEEP TRANSCRANIAL MAGNETIC STIMULATION

CROSS REFERENCE TO RELATED APPLICATIONS

The present application is a continuation-in-part application of U.S. patent application Ser. No. 13/772,449, filed on Feb. 21, 2013, issued as U.S. Pat. No. 9,248,308 on Feb. 2, 2016.

FIELD OF THE INVENTION

The present invention relates to a family of deep transcranial magnetic stimulation (TMS) coils, wherein a stimulating portion of the coils is at least partially circular and is configured to encircle at least a section of a body organ.

BACKGROUND OF THE INVENTION

Transcranial magnetic stimulation (TMS) is a noninvasive technique used to apply brief magnetic pulses to the brain, or to other human organs, and to thereby activate neuronal structures. The pulses are administered by passing high currents by a stimulator through an electromagnetic coil externally placed upon the patient (for example, placed on the scalp for brain treatment), inducing electrical currents in the underlying tissue, thereby producing a localized axonal depolarization. This technique has become a major tool in central nervous system research, as well as a potentially promising treatment option for various neurobehavioral and neurological disorders.

Most known TMS coils stimulate superficial brain regions in the brain cortex, but the rate of decay of the induced magnetic and electric field as a function of distance from the coil is high. Hence the efficacy of affecting deeper neuronal structures is low. Stimulating deeper neuronal structures may be feasible if the intensity of the induced field is greatly increased. Yet operation at such increased intensity may increase the risk for seizures and for physiological damage to the tissue.

A method for deep brain TMS with minimal stimulation of superficial regions is disclosed in U.S. Pat. No. 7,407,478, wherein deep brain stimulation is made possible while minimizing side effects. The device described therein includes a base and an extension portion, the base having individual windings for individual paths of current flow, and the extension portion designed so as to minimize unwanted stimulation of other regions of the brain.

However, there is a need for more specifically designed coils, which can target particular areas of the brain including deep neuronal structures with minimal effect on other brain regions. Examples of specific brain regions that may be desired to be stimulated are frontal lobe regions, occipital lobe regions, parietal lobe regions, right temporal regions and left temporal regions. Other examples may include activation of brain regions including deeper brain regions in a certain circumference of the brain, such as around a particular axial slice.

Thus, there is a need for specifically designed coils for deep TMS which are location-specific for frontal lobe, occipital lobe, parietal lobe or temporal lobe brain regions. The coils must induce the desired distribution of the electric field in the brain, and simultaneously induce electric field intensity in the relevant brain tissue which will be feasible for neuronal stimulation with available TMS stimulators for most of the population. The stimulation intensity is routinely calibrated individually for each subject based on his or her motor threshold. Hence the coil efficiency must guarantee that the motor threshold and stimulation intensity for most of the relevant population is within an acceptable range with respect to available stimulators power outputs.

The coils design must be efficient with respect to energy consumption, coil heating rate, compact size and ease of operation.

SUMMARY OF THE INVENTION

There is provided, in accordance with one embodiment of the present invention, a coil for transcranial magnetic stimulation. The coil includes a base portion having substantially parallel multiple stimulating elements, wherein the base portion is configured to encircle at least a portion of a first section of a body part and to provide electrical flow in a substantially circular path, and a return portion having substantially parallel multiple return elements, wherein the return portion is configured to encircle at least a portion of a second section of the body part which is different than the first section, and to provide electrical flow in a continuation of the substantially circular path of the base portion.

In embodiments of the present invention, the base portion is complementary to the human head or head portion, or to another body organ. The base has a flexibility that allows it to conform to the relevant body organ (such as the human head or head portion).

The base includes individual stimulating elements carrying electric current in one or more common directions, referred to herein as a "main direction." In this main direction, the main physiologic effect (such as neuronal stimulation) is induced in the body organ. The elements are not dense together at a narrow segment, but are rather distributed at various locations around the body organ. In some embodiments the individual elements are evenly distributed across the base. In other embodiments some or all the elements may be grouped in two or more groups with certain distances between the groups. The spacing between adjacent elements may be uniform, variable, periodic or other. In embodiments where some or all the elements are grouped in groups, the spacing between adjacent groups or between a group and an adjacent element, and the breadth of each group, may be uniform across the base, variable, periodic or other. Any combination or arrangement of elements is included within the scope of the invention, with a particular feature being that the elements are not crowded together in a narrow segment.

The individual elements in the base carrying current in the main direction are all or mostly tangential to the relevant body organ (such as a portion of a human skull), at all or a substantial part of their path. In order to optimize the efficacy of activation in deeper brain regions, it is desirable to minimize the non-tangential components of the induced electric field. Since the induced electric field orientation is in general parallel to the orientation of the elements carrying alternating currents, it is desirable to minimize the portions of coil elements which are non-tangential to the body organ (such as a human skull), especially in the base and its vicinity.

Coil elements carrying electric current in a direction opposite to the one or more main directions, are placed remote from the base. These elements are referred to herein as "return elements." In some embodiments, the return elements are located adjacent to other body organs or other portions of a body organ (such as other head regions), relative to the base. These return elements are termed "contacting return elements." In other embodiments, the return elements are located at a certain distance from the body and are not configured to contact the body. These return elements are termed "protruding return elements." In some embodiments, some of the return elements are contacting and some of them are protruding.

The stimulating elements encircle a body organ (such as a human head or head portion). In some embodiments, the coil includes a single base which conforms to the head or other body organ in a certain region. In some embodiments, the base is adjacent to the frontal cortical region, while in other embodiments, the base is adjacent to the occipital region, temporal region or parietal region of the skull. In some embodiments, the base includes multiple portions, wherein each portion conforms to a different region of the body organ, such as the head. Spacing between adjacent elements may be different within one base portion than within another base portion.

Return elements are located remote from the base or from specific portions of the base. In some embodiments, return elements surround the body part (such as the head) as a continuation and in a similar plane to the base elements. For example, in some embodiments, the base elements may be adjacent to a frontal head region and the return elements may be adjacent to an occipital head region. Connecting elements connecting stimulating elements to return elements may run along the temporal lobe on the right and left hemispheres, for example. In some embodiments, return elements may run in a different plane than stimulating elements. For example, stimulating elements of the base may be adjacent to occipital head regions, while return elements run along parietal head regions. In some embodiments, return elements contact head regions which are remote from stimulating elements. In some embodiments, all stimulating elements and/or all return elements are contacting elements, while the spacing between elements and the density of elements may vary in different regions. In some embodiments, return elements are protruding elements. In yet other embodiments, some of the return elements are contacting and some are protruding. Similarly, connecting elements may be contacting, protruding, or partially contacting and partially protruding.

The definition of the base relates to the functional elements of the coil carrying electric currents. However, there is no limitation regarding other elements of the device, such as mechanical components, cases and covers. Thus, certain elements of the base may be encased in a case containing additional coil elements such as return elements and other elements.

The coil must induce the desired distribution of the electric field in the brain, and simultaneously induce an electric field intensity in the relevant brain tissue which is high enough to induce neuronal stimulation.

Several features of the coil are important in order to achieve the above goals. These include:

1. Arrangement of the base portion elements. This arrangement must be optimized for each coil design and each specific goal. An interplay between two competing ideals may take place: Better depth penetration profile, namely higher relative electric field in the deeper target brain region compared to superficial region, on one hand, and higher absolute electric field intensity in the target brain region on the other hand. As a non-limiting example, suppose a base portion contains two groups of elements with a certain distance d between them. Increasing d will improve the depth penetration profile but may reduce the absolute field intensity in the target brain region. The intensity must be such that it will enable induction of the desired physiological effect in the target neural structures in the majority of the population with stimulators available in the market. Hence the distance d—as well as other configuration parameters—must be optimized for each coil design.

2. Location of the return portions relative to the base portion. The distance between the portions must be optimized for each design: Too short a distance will lead to reduction of the total induced electric field in the target brain region, due to the effect of the return elements. Too long a distance will require long connecting coil elements and their effect must be taken into account. Furthermore, the coil size must be optimized for easy location, navigation and placement over the head.

3. Location of the return portions relative to the brain. The return elements affect closer brain regions. The location of the return portions must consider their effect on any brain structure and the design must lead to minimal undesired side effects such as motor activation or pain.

4. The type of the return elements. Return elements may be either contacting or protruding as defined above. The ratio between contacting and protruding return elements is very important in various aspects and must be optimized for each specific coil design. In general, protruding elements induce electrostatic charge accumulation on the brain surface. This leads to reduction in the absolute electric field induced in the target brain regions, and also reduction in the relative intensity of the electric field in deeper brain regions compared to superficial regions. On the other hand, contacting elements may increase the effect in adjacent brain regions. Hence a delicate optimization must be performed in each case.

5. The distance of protruding return elements from the head, in coils containing protruding return elements. Longer distance reduces the direct effect of the return elements on the brain, but increases the charge accumulation due to the presence of longer non-tangential coil elements which are connected to the return elements and move them away from the head. A delicate optimization must be performed in each case to account for this effect.

6. The overall coil inductance. The number, length, configuration and packing parameters of the coil windings must be planned to lead to coil inductance in the desired range. Usually the desired range for TMS coils inductance is between 15 and 30 microHenri. Too high inductance may reduce coil efficacy, increase pulse width and is often associated with increased coil resistance, energy consumption and coil heating. Too small inductance may lead to fast rate of change of the electric current which may damage stimulator components.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The above and further advantages of the present invention may be better understood by referring to the following description in conjunction with the accompanying drawings in which.

Figure 1:
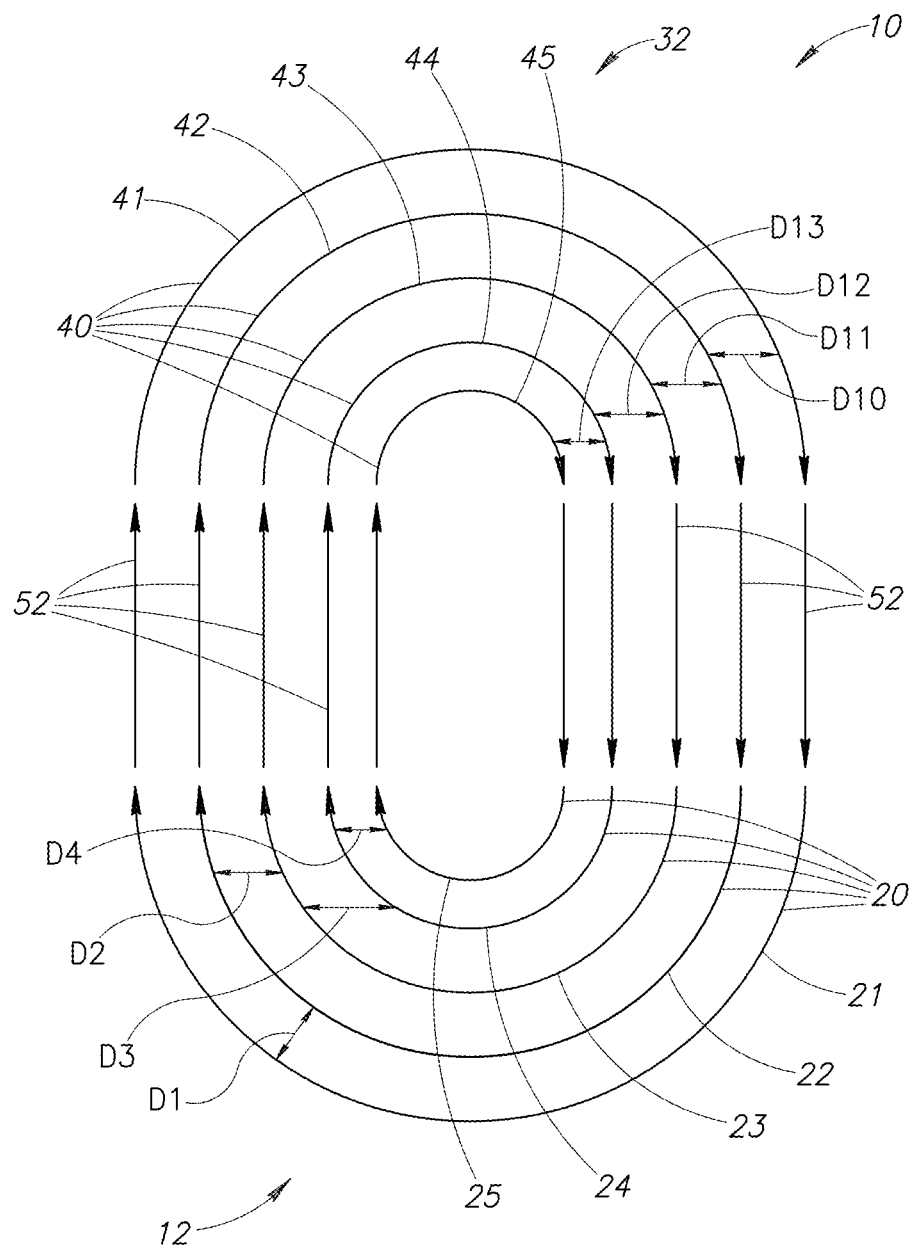
FIG. 1 is a schematic illustration showing principles of stimulation for circular coils, in accordance with embodiments of the present invention.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION OF THE INVENTION

In the following detailed description, numerous specific details are set forth in order to provide a thorough understanding of the present invention. It will be understood by those of ordinary skill in the art that the present invention may be practiced without these specific details. In other instances, well-known methods, procedures, components and structures may not have been described in detail so as not to obscure the present invention.

The present invention is directed to circular coils for deep TMS and methods of use thereof. The principles and operation of systems and methods according to the present invention may be better understood with reference to the drawings and accompanying descriptions.

Before explaining at least one embodiment of the present invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

Reference is now made to FIG. 1, which is a schematic illustration showing principles of stimulation for circular coils, in accordance with embodiments of the present invention. In the embodiment shown in FIG. 1, a schematic illustration of a circular coil depicts the elements of a circular coil in accordance with embodiments of the present invention, but does not depict the actual appearance of these elements. As shown in FIG. 1, circular coil 10 includes a base portion 12 and a return portion 32. A "circular coil" is defined as a coil wherein base portion 12 encircles at least a portion of the body part and return portion 32 encircles at least a portion of the body part. "Encircling" may include encircling in contact with the body part or protruding at a distance from the body part. Base portion 12 and return portion 32 are depicted schematically in FIG. 1 as being semi-circular in shape. However, it should be readily apparent that other shapes are possible and may also be configured to encircle a body part in accordance with embodiments of the present invention, as will be described further hereinbelow—for example with reference to FIG. 2B. Base portion 12 includes multiple stimulating elements 20, depicted in FIG. 1 with arrows to illustrate the direction of electrical flow. Multiple stimulating elements 20 are shown as individual stimulating elements labeled first stimulating element 21, second stimulating element 22, third stimulating element 23, fourth stimulating element 24 and fifth stimulating element 25. It should be readily apparent that although five individual stimulating elements are shown in FIG. 1 schematically, circular coil 10 may include any suitable number of stimulating elements and are not limited to the amounts shown herein. Multiple stimulating elements 20 are substantially parallel to one another and are spaced apart from one another by distances, wherein first and second stimulating elements 21 and 22 are separated by a first stimulating distance D1, second and third stimulating elements 22 and 23 are separated by a second stimulating distance D2, third and fourth stimulating elements 23 and 24 are separated by a third stimulating distance D3, fourth and fifth stimulating elements 24 and 25 are separated by a fourth stimulating distance D4, and so on. Stimulating distances D1, D2, D3, etc. may be equal to one another or may vary in a random or periodic manner. The direction of electrical stimulation of each of stimulating elements 20 is substantially the same and is at least partially circular. That is, current flows through each of multiple stimulating elements in a curved or circular path, and multiple stimulating elements 20 are nested within one another, such that current flows in the same curved or circular path for each of stimulating elements 21-25 but separated by distances D1-D4.

Return portion 32 includes multiple return elements 40. Return elements 40 are depicted in FIG. 1 with arrows to illustrate the direction of electrical flow. Multiple return elements 40 are shown as individual return elements labeled first return element 41, corresponding to first stimulating element 21, second return element 42 corresponding to second stimulating element 22, third return element 43 corresponding to third stimulating element 23, fourth return element 44 corresponding to fourth stimulating element 24 and fifth return element 45 corresponding to fifth stimulating element 25. It should be readily apparent that although five individual return elements are shown in FIG. 1 schematically, circular coil 10 may include any suitable number of return elements and are not limited to the amounts shown herein. Generally, the number of return elements 40 corresponds to the number of stimulating elements 20. Multiple return elements 40 are substantially parallel to one another and are spaced apart from one another by distances, wherein first and second return elements 41 and 42 are separated by a first return distance D10, second and third return elements 42 and 43 are separated by a second return distance D11, third and fourth stimulating elements 43 and 44 are separated by a third return distance D12, fourth and fifth return elements 44 and 45 are separated by a fourth return distance D13, and so on. Return distances D10, D11, D12, etc. may be equal to one another or may vary in a random or periodic manner. It should be readily apparent from FIG. 1 that the direction of electrical flow for return elements 40 is a continuation of the circular path of electrical flow for stimulating elements 20. Thus, if electrical flow for stimulating elements 20 is in a clockwise direction, electrical flow for return elements 40 is also in a clockwise direction. If electrical flow for stimulating elements 20 is in a counter-clockwise direction, electrical flow for return elements 40 is also in a counter-clockwise direction. In some embodiments, stimulating elements 20 are electrically connected to return elements 40 via connecting elements 52. As shown in FIG. 1, connecting elements 52 carry electrical flow in the same clockwise or counterclockwise direction as stimulating elements 20 and return elements 40.

Figure 2A:
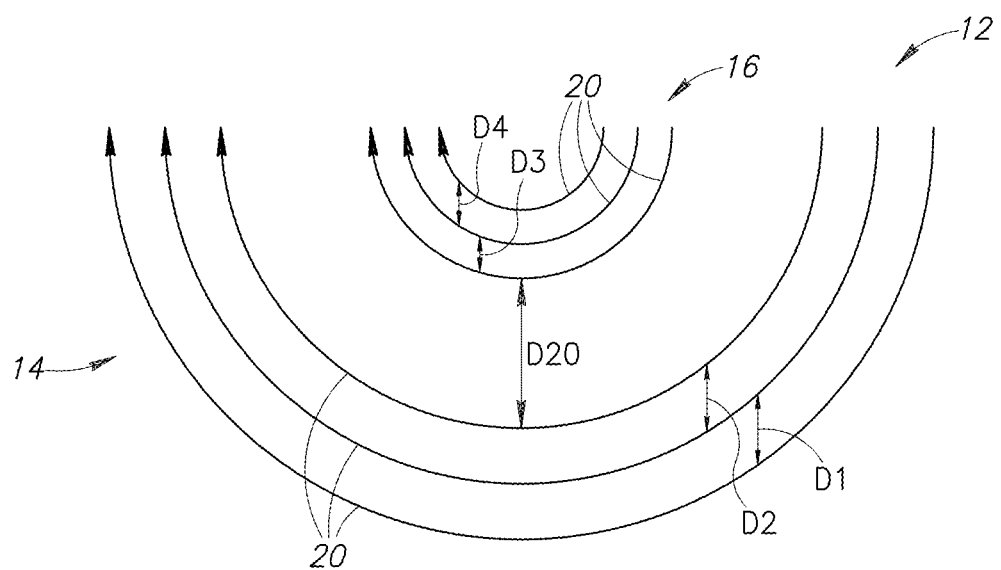
FIGS. 2A-2C are schematic illustrations of a base portion of the circular coil of FIG. 1, in accordance with embodiments of the present invention.
Figure 2B:
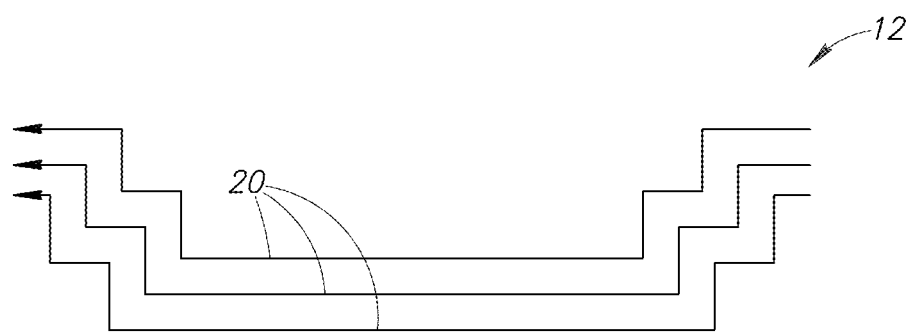

Reference is now made to FIGS. 2A and 2B, which are schematic illustrations of base portion 12 in accordance with embodiments of the present invention. In one embodiment, as shown schematically in FIG. 2A, base portion 12 includes a first base portion group 14 and a second base portion group 16. First base portion group 14 may be separated from second base portion group 16 by a first base portion group distance D20. In some embodiments, additional base portion groups may be included as well, and separated from one another by additional base portion group distances. Each base portion group is defined as a group by one of several criteria, including location, spacing, and connection to return elements. For example, first base portion group 14 may include multiple stimulating elements each separated by equal distances D1 and D2, while second base portion group 16 may include multiple stimulating elements separated from one another by equal distances D3 and D4, wherein D1 and D2 are different than D3 and D4. In another embodiment, first base portion group 14 may be configured to be positioned on one portion of the head while second base portion group 16 may be configured to be positioned on another portion of the head. In yet another embodiment, first base portion group 14 may be connected to return elements which are in contact with the head and second base portion group 16 may be connected to return elements which are protruding from the head. It should be readily apparent that a direction of current flow in first base portion group 14 is substantially the same as a direction of current flow in second base portion group 16.

Figure 2C:
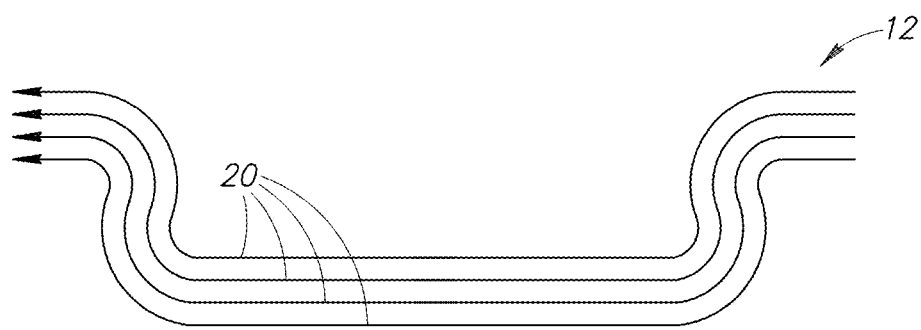

Reference is now made to FIGS. 2B and 2C, which are illustrations of base portion 12 in accordance with additional embodiments of the present invention. In the embodiments shown herein, base portion 12 includes multiple stimulating elements 20 which follow a modified curved path. For example, as shown in FIG. 2B, each of multiple stimulating elements 20 is configured in a step formation on two ends of a substantially semi-circular path. As another example, as shown in FIG. 2C, each of multiple stimulating elements 20 is configure in a partially outwardly curved and partially straight formation. Many other configurations are possible. In all of the embodiments, multiple stimulating elements are configured to conform to the shape of the body part, such as the head, and to encircle at least a portion of the body part.

Figure 3A:
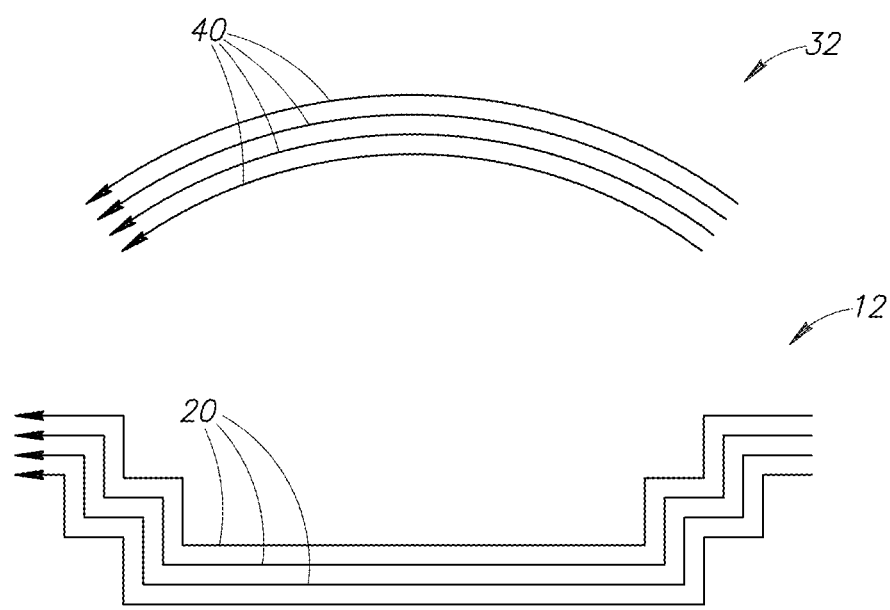
FIGS. 3A and 3B are schematic illustrations of base portions and return portions of the circular coil of FIG. 1, wherein the base and return portions have various configurations in accordance with embodiments of the present invention.
Figure 3B:
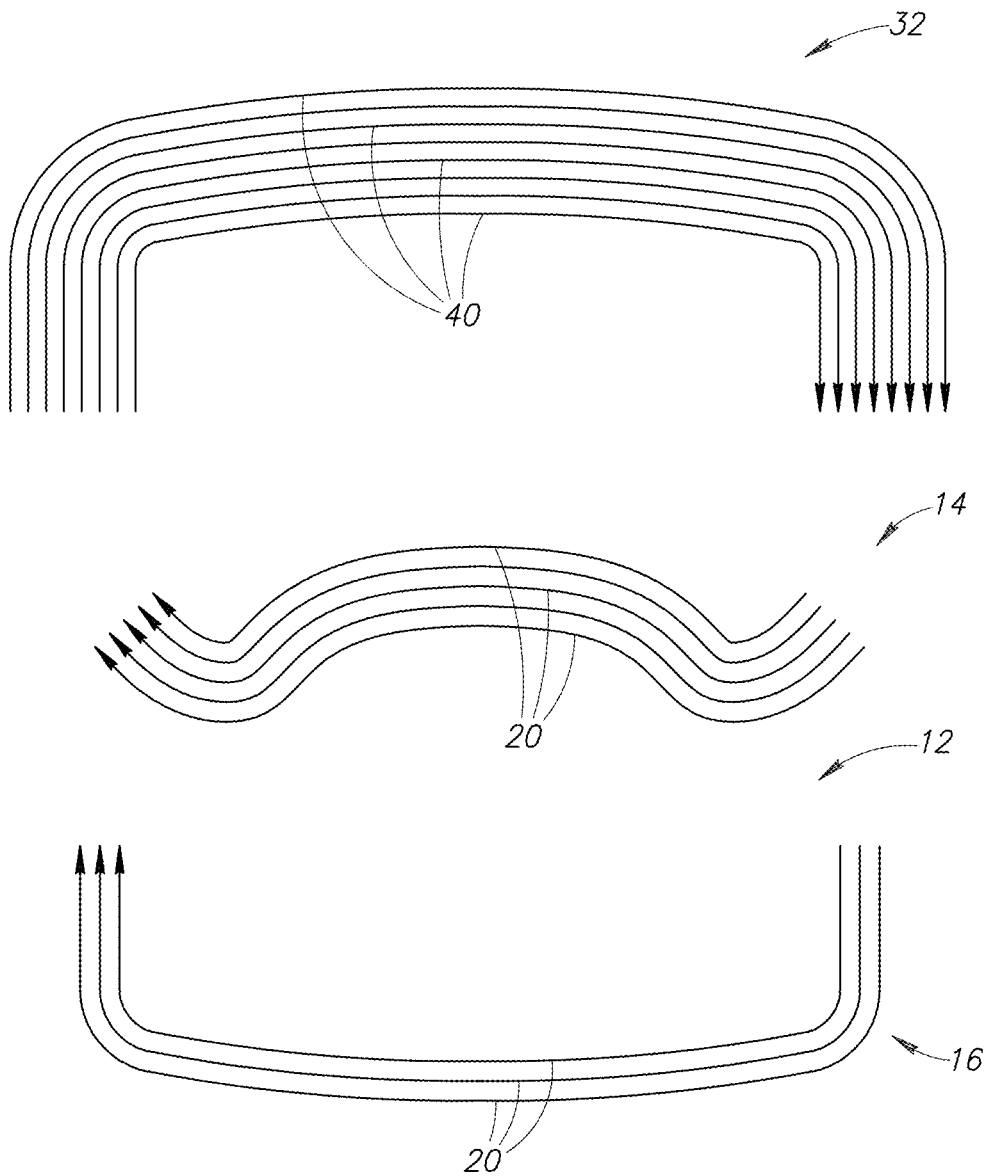

Return portion 32 may follow a similar pattern as base portion 12 or may have a different configuration. For example, as shown in FIGS. 3A, base portion 12 may include a step configuration while return portion 32 may be semi-circular. As another example, as shown in FIG. 3B, base portion 12 may include a first base portion group 14 having a first configuration and a second base portion group 16 having a second configuration, while return portion 32 has a single configuration for all of return elements 40. Alternatively, return portion 32 may include multiple return portion groups.

Figure 4:
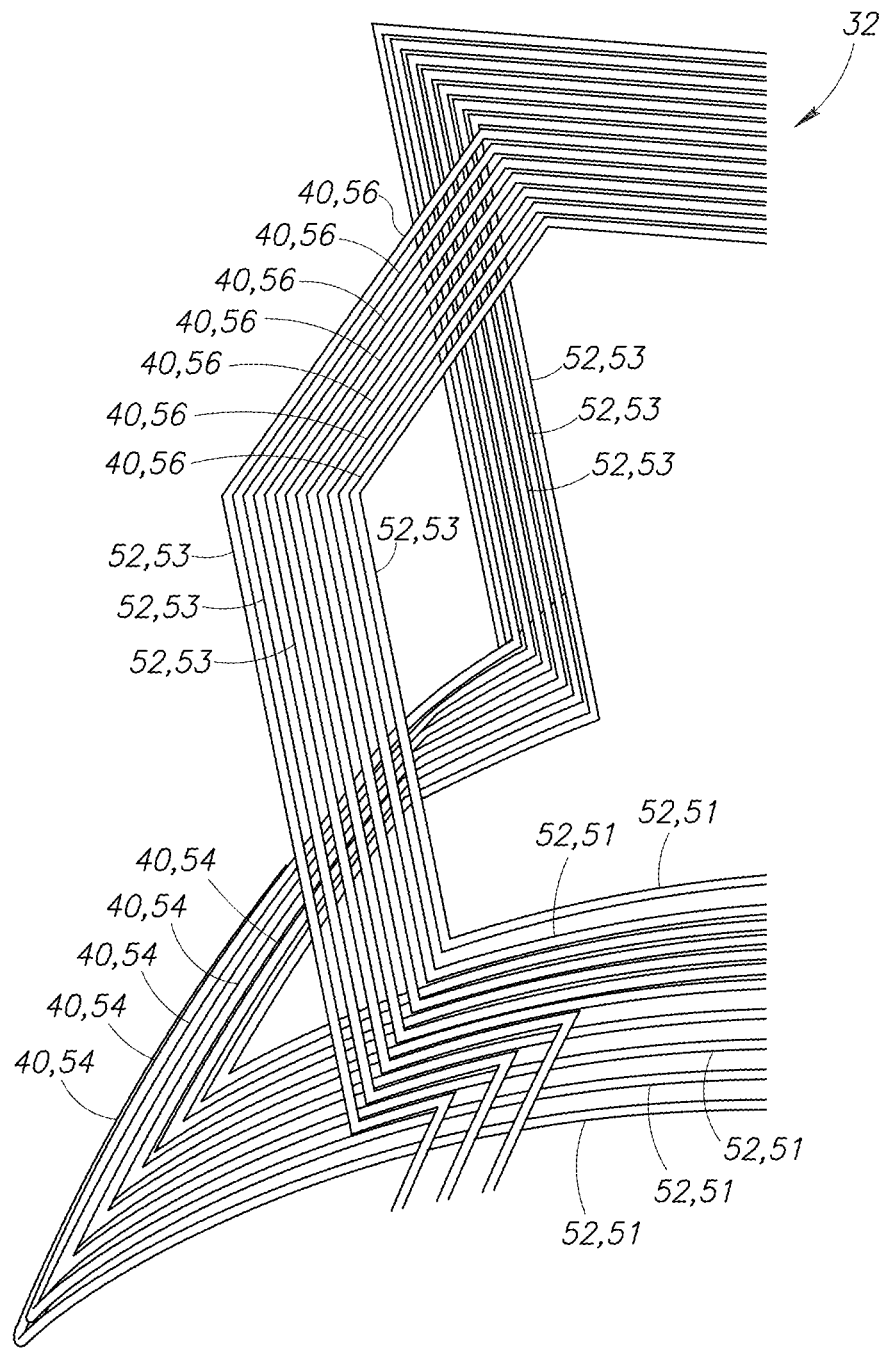
FIG. 4 is an illustration of a return portion of the circular coil of FIG. 1, in accordance with embodiments of the present invention.

Reference is now made to FIG. 4, which is an illustration of a return portion 32, in accordance with embodiments of the present invention. Depicted in FIG. 4 is a return portion 32 configured to be positioned on a side of the head, although it should be readily apparent that similar configurations of return portion 32 may be used for other areas, such as a rear portion of the head, for example. Return elements 40 are shown at two different heights, wherein some of return elements 40 are configured to be in contact with a body part and are on a same plane as base portion 12 (not shown). These return elements 40 are referred to as contacting return elements 54. Some of return elements 40 are configured to be protruding from the plane of base portion 12, and are referred to as protruding return elements 56. Protruding return elements 56 may be at a vertical distance or a horizontal distance (i.e., on the same plane or on a different plane) from base portion 12, as long as protruding return elements 56 are configured to protrude from circular coil 10 such that they are configured not to contact the body part which base portion 12 is configured to contact. Thus, connecting elements 52 may be horizontal connecting elements 51 or may be vertical connecting elements 53 or may have additional configurations as needed to connect return portion 32 to base portion 12.

In some embodiments, some of multiple return elements 40 are contacting return elements 54 and some of multiple return elements 40 are protruding return elements 56. In some embodiments, all of multiple return elements 40 are contacting return elements 54. In some embodiments all of multiple return elements 40 are protruding return elements 56. Any combination of protruding and/or contacting return elements is possible and is included within the scope of the present invention.

Figure 5:
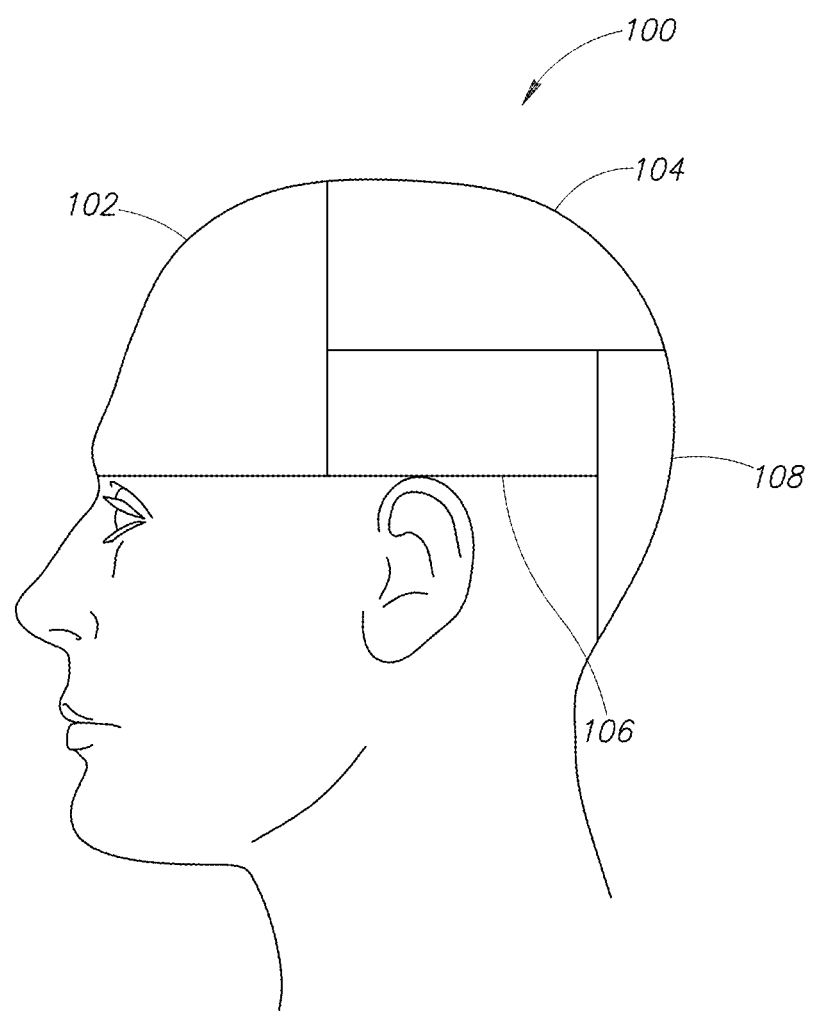
FIG. 5 is an illustration of anatomical sections of a head.

Reference is now made to FIG. 5, which is an illustration of anatomical sections of a head 100. For the purposes of illustrating the present invention, head 100 has four sections: a frontal section 102 at a front portion of head 100, a parietal section 104 to the rear of frontal section 102 and at a top portion of head 100, a temporal section 106 on the side of head 100 and an occipital section 108 at a rear portion of head 100. Circular coil 10 is configured such that base portion 12 with stimulating elements 20 are positionable on and at least partially encircle a first section of head 100, and return portion 32 with return elements 40 are positionable on and at least partially encircle a second section of head 100 which is different than the first section. Thus, for example, base portion 12 may be positioned on frontal section 102 and return portion 32 on parietal section 104. Alternatively, base portion 12 may be positioned on parietal section 104 and return portion positioned on occipital section 108. In other examples base portion 12 may be positioned on frontal section 102 and return portion 32 on occipital section 108. In this way, base portion 12 stimulates a section of the brain, while return portion brings returning current back at a section which is remote from the stimulated section of the brain. In some embodiments, both base portion 12 and return portion 32 are adjacent to the head, and in some embodiments, base portion 12 is adjacent to the head while return portion 32 is remote from the head. In some embodiments, connecting elements 52 are adjacent to the head and in other embodiments, connecting elements 52 are remote from the head.

Figure 6:
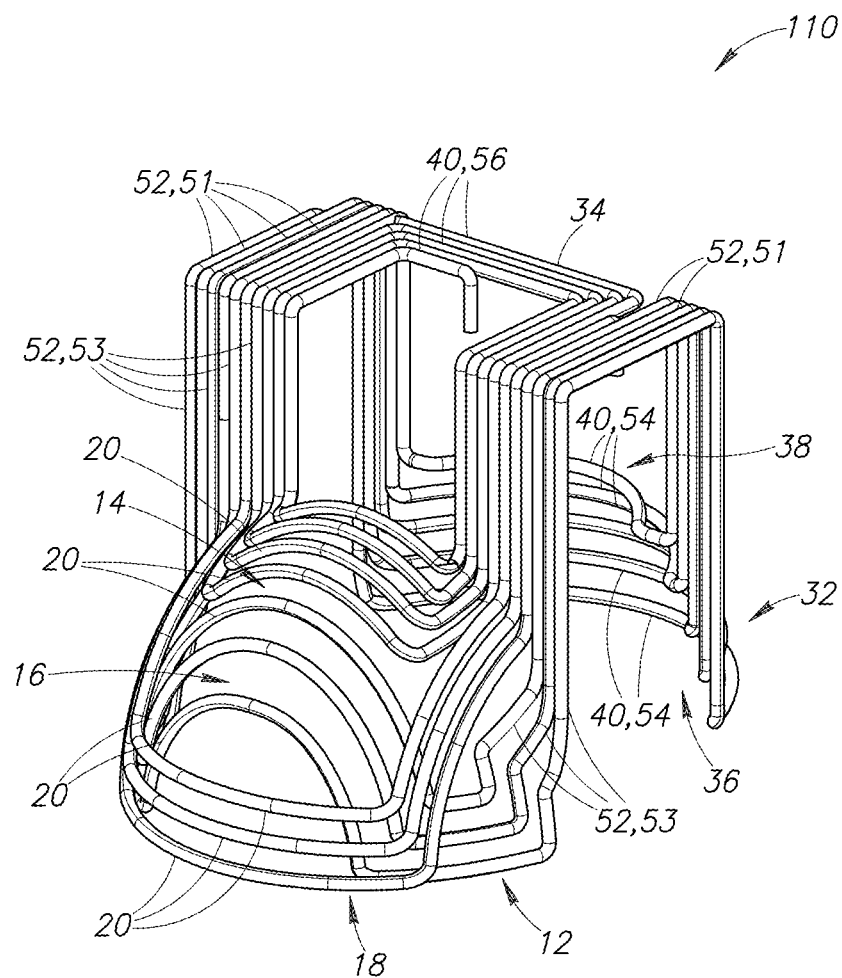
FIG. 6 is a perspective illustration of a coil which is an example of the circular coil of FIG. 1, in accordance with embodiments of the present invention.

Reference is now made to FIG. 6, which is a perspective illustration of a coil 110 which is an example of a circular coil 10 in accordance with embodiments of the present invention. Coil 110 includes a base portion 12 having a first base portion group 14 of multiple stimulating elements 20, a second base portion group 16 of multiple stimulating elements 20 and a third base portion group 18 of multiple stimulating elements 20. Coil 110 further includes a return portion 32 including return elements 40 corresponding to multiple stimulating elements 20. Thus, return portion 32 also includes a first return portion group 34 corresponding to first base portion group 14, a second return portion group 36 corresponding to second base portion group 16, and a third return portion group 38 corresponding to third base portion group 18. In the embodiment shown herein, base portion 12 is configured to be positioned on a frontal section 102 of head 100 and return portion 32 is configured to be positioned on an occipital section 108 of head 100. First base portion group 14 is positioned at a top portion of base portion 12, and first return portion group 34, corresponding to first base portion group 34, is comprised of protruding return elements 56. Second base portion group 16 is positioned below first base portion group 14, and distances between multiple stimulating elements 20 of second base portion group 16 are greater than distances between multiple stimulating elements 20 of first group 14. Second return portion group 36 corresponding to first base portion group 16 is comprised of contacting return elements 54, which are configured to contact and at least partially encircle an occipital section 108 of head 100. Third base portion group 18 is positioned below first and second base portion groups 14 and 16, and includes multiple stimulating elements 20 which have a different shape than multiple stimulating elements 20 of first and second base portion groups 14 and 16. Third return portion group 38 corresponding to third base portion group 18 is comprised of contacting return elements 54 and is positioned above second return portion group 36. Third return portion group 38 is also configured to be positioned on occipital section 108 of head 100. Connecting elements 52 include vertical connecting elements 53 and horizontal connecting elements 51 wherein horizontal connecting elements 51 protrude from base portion 12.

Coil 110 is used to stimulate lateral and medial prefrontal and orbitofrontal brain regions with a bilateral symmetry, and may be useful for treating, for example, Alzheimer's disease.

Figure 7:
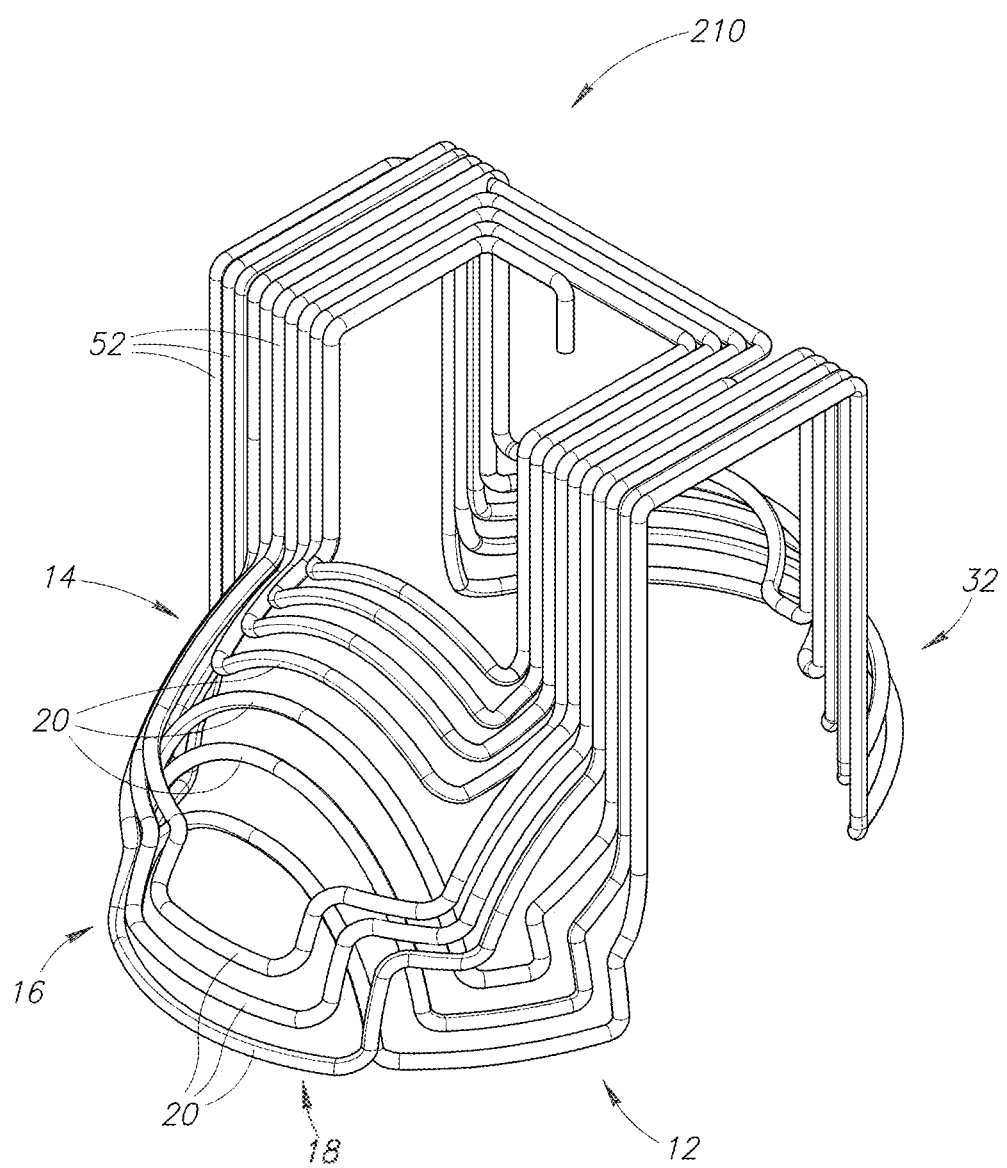
FIG. 7 is a perspective illustration of a coil which is an example of the circular coil of FIG. 1, in accordance with embodiments of the present invention.

Reference is now made to FIG. 7, which is a perspective illustration of a coil 210, which is an example of a circular coil 10 in accordance with embodiments of the present invention. Coil 210 is similar in construction to coil 110. However, third base portion group 18 of coil 210 has a different configuration than third base portion group 18 of coil 110. Third base portion 18 of coil 210 has a step configuration such as that shown in FIG. 2B.

Coil 210 is used to stimulate lateral and medial prefrontal and orbitofrontal brain regions with a bilateral symmetry, and may be useful for treating, for example, Alzheimer's disease.

Figure 8:
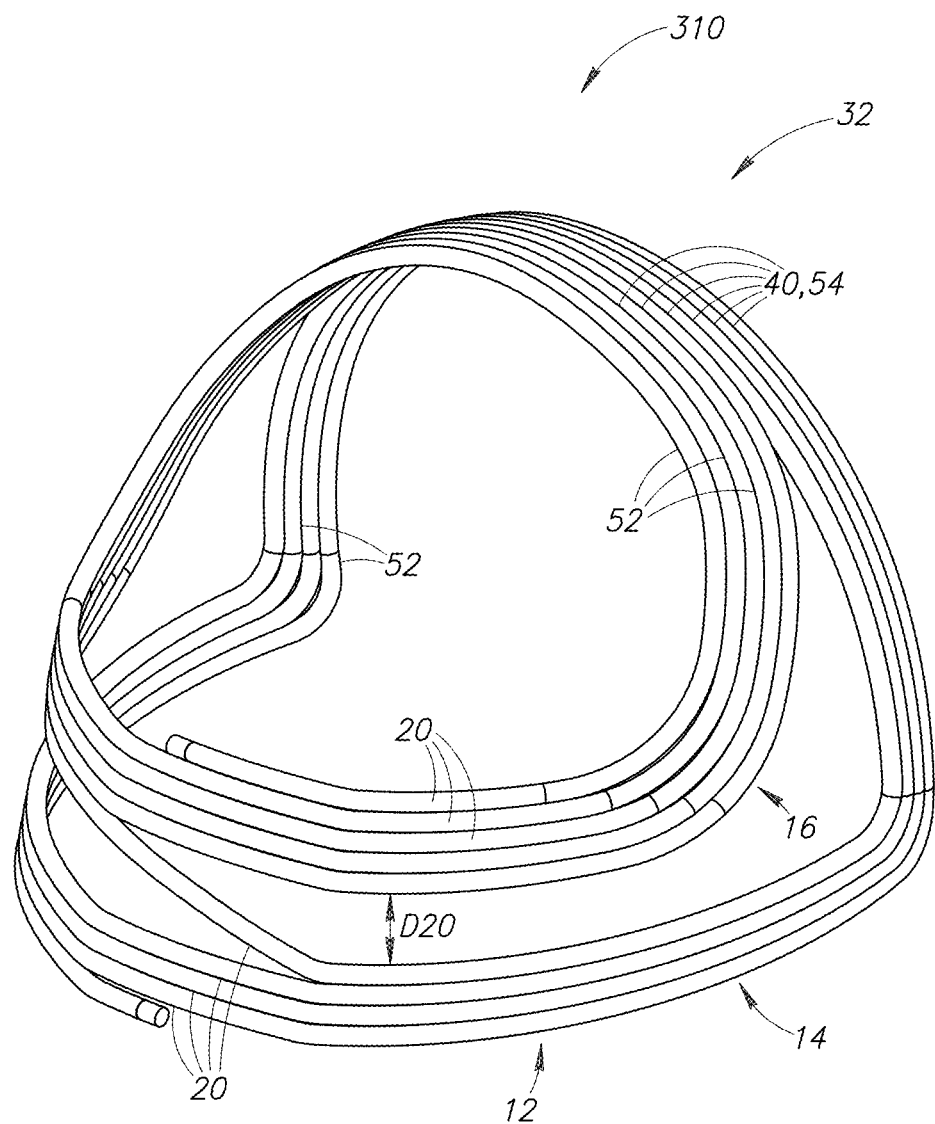
FIG. 8 is a perspective illustration of a coil which is an example of the circular coil of FIG. 1, in accordance with embodiments of the present invention.

Reference is now made to FIG. 8, which is a perspective illustration of a coil 310, which is an example of a circular coil 10 in accordance with embodiments of the present invention.

Coil 310 includes a base portion 12 having a first base portion group 14 of multiple stimulating elements 20 and a second base portion group 16 of multiple stimulating elements 20. Coil 310 further includes a return portion 32 including return elements 40 corresponding to multiple stimulating elements 20. In the embodiment shown herein, base portion 12 is configured to be positioned on an occipital section 108 of head 100 and return portion 32 is configured to be positioned on a top of parietal section 104 of head 100. Alternatively, base portion 12 may be positioned on a parietal section 104 and return portion may be positioned on an occipital portion 108 of head 100. First base portion group 14 is positioned at a lower portion of base portion 12 and second base portion group 16 is positioned higher than first base portion group 14 and is separated from first base portion group 14 by a distance D20. Return elements 40 of return portion 32 are contacting return elements 54, which are configured to contact and at least partially encircle portion of head 100. Connecting elements 52 are configured to contact the head as well.

Coil 310 is used to stimulate occipital brain regions and regions in the cerebellum and may be useful for treating, for example, Parkinson's disease or migraine.

Figure 12:
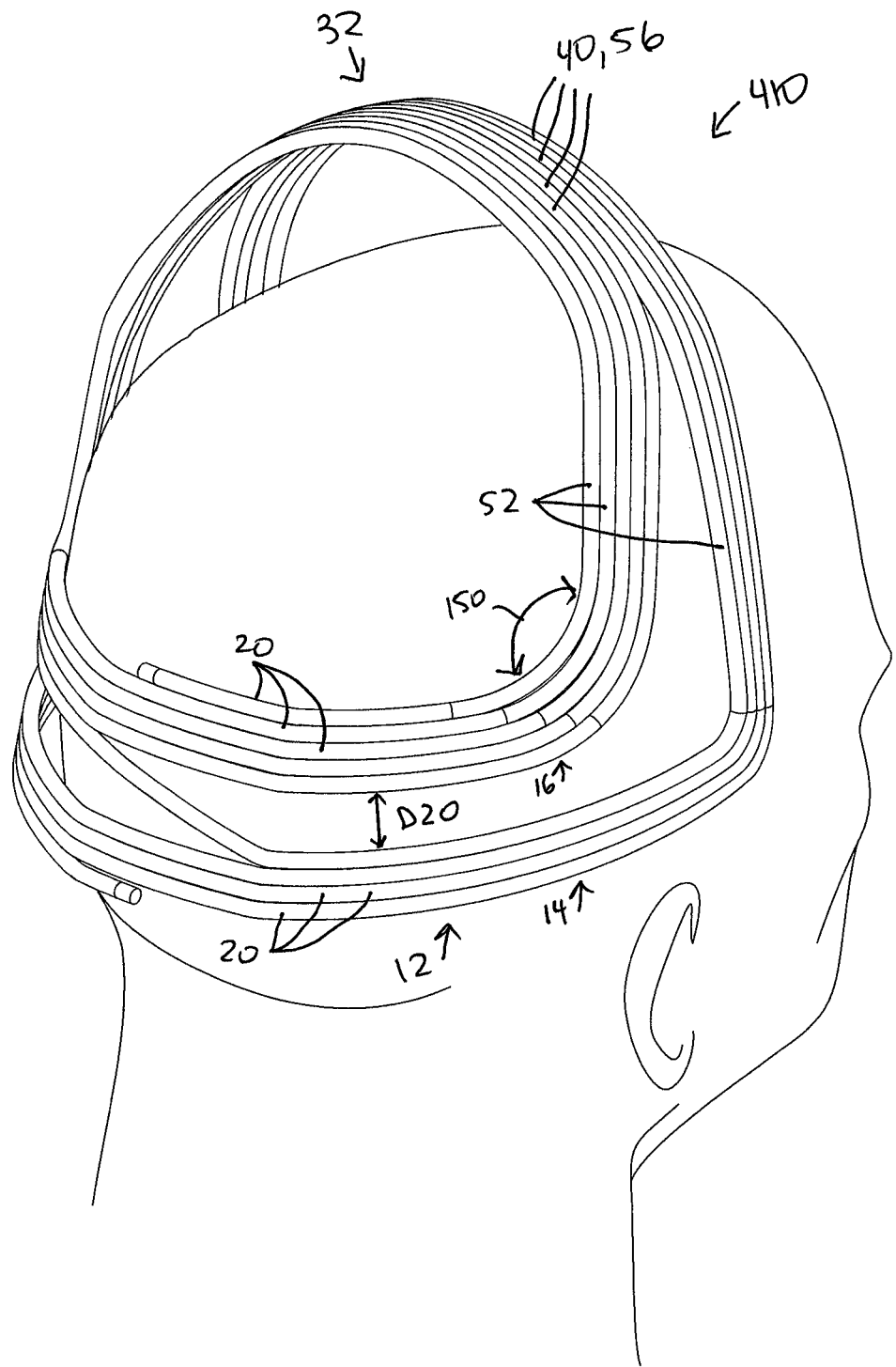
FIG. 12 is a perspective illustration of a coil which is an example of the circular coil of FIG. 1, in accordance with embodiments of the present invention.

Reference is now made to FIG. 12, which is a perspective illustration of a coil 410, which is an example of a circular coil 10 in accordance with embodiments of the present invention.

Coil 410 is similar to coil 310 as depicted in FIG. 8, but instead of return elements being contacting return elements, return elements 40 are protruding return elements 56. Connecting elements 52 may be contacting or protruding. However, a length of connecting elements is such that when stimulating elements are positioned on the first portion of the skull, return elements are protruding therefrom. For example, connecting elements may have a length of at least 10 cm, such that return elements are configured to protrude from the head.

Coil 410 includes a base portion 12 having a first base portion group 14 of multiple stimulating elements 20 and a second base portion group 16 of multiple stimulating elements 20. Coil 310 further includes a return portion 32 including return elements 40 corresponding to multiple stimulating elements 20. In the embodiment shown herein, base portion 12 is configured to be positioned on an occipital section 108 of head 100 and return portion 32 is configured to be positioned surrounding parietal section 104 of head 100. Alternatively, base portion 12 may be positioned on a parietal section 104 and return portion may be positioned surrounding occipital portion 108 of head 100. First base portion group 14 is positioned at a lower portion of base portion 12 and second base portion group 16 is positioned higher than first base portion group 14 and is separated from first base portion group 14 by a distance D20. Return elements 40 of return portion 32 are protruding return elements 56, which are configured to protrude from and at least partially encircle portion of head 100. Connecting elements 52 are configured to contact the head as well. Connecting elements 52 are at an angle of less than 180 degrees to stimulating elements 20, as depicted by arrows 150. Thus, return elements 40, which run across from connecting elements on one side to connecting elements on the other side of base portion 12, are also at an angle to stimulating elements 20. In the embodiment shown herein, the angle is approximately 90 degrees.

Coil 410 is used to stimulate brain structures in the occipital cortex and the cerebellum.

Figure 13A:
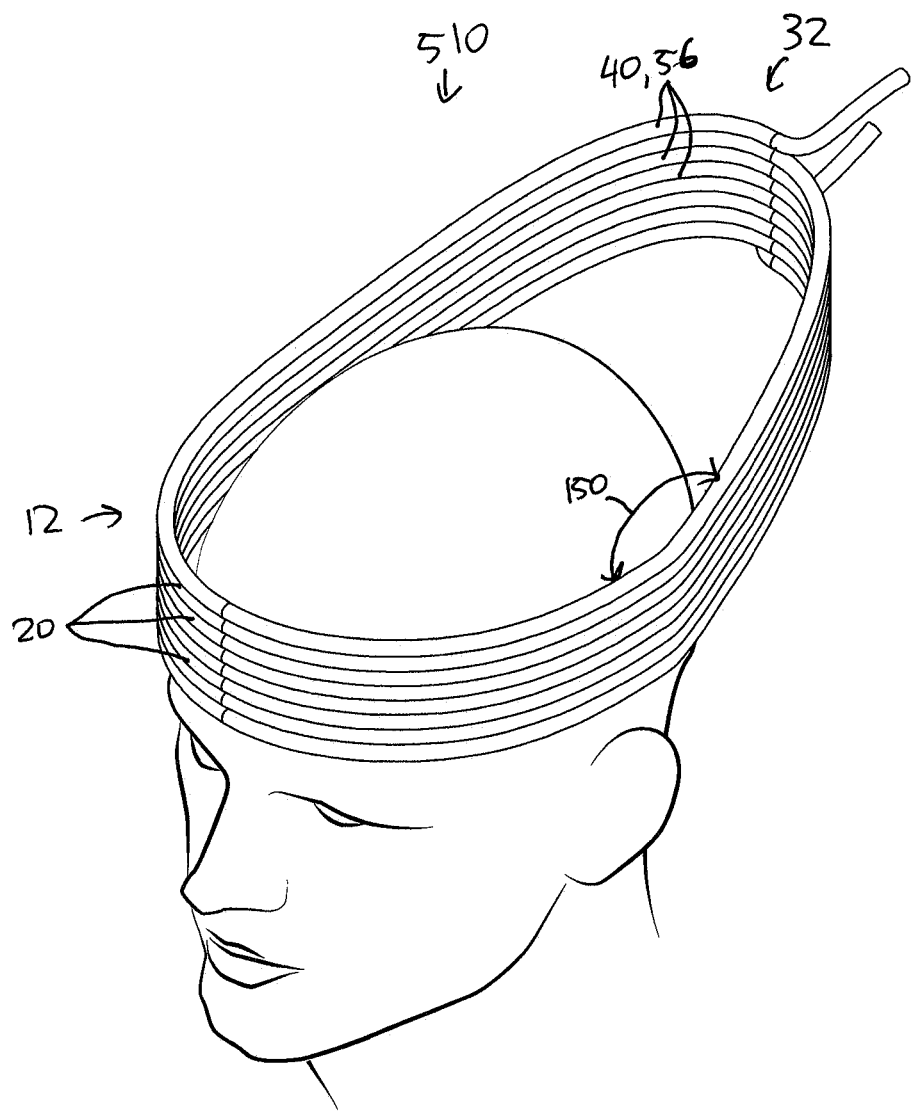
FIGS. 13A-13D are perspective illustrations of a coil which is an example of the circular coil of FIG. 1, in accordance with embodiments of the present invention depicted in various forms and from different sides.
Figure 13B:
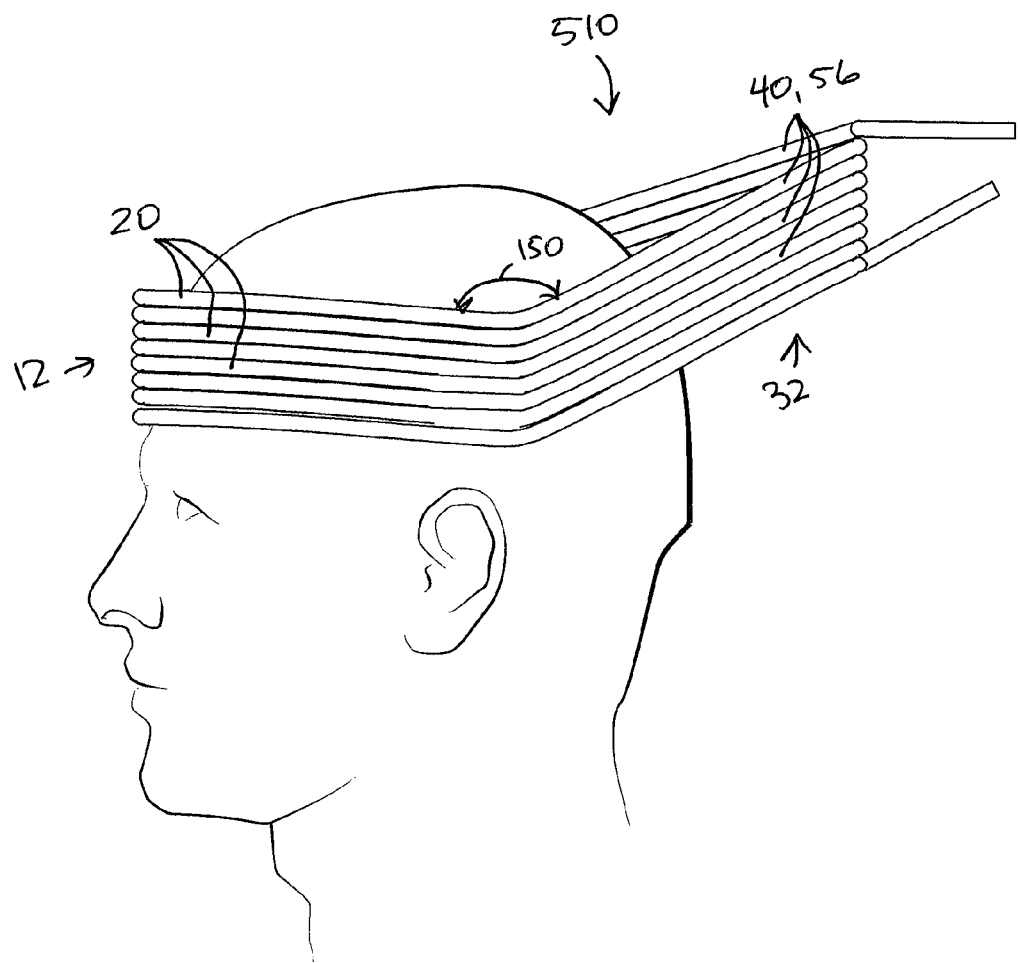
Figure 13C:
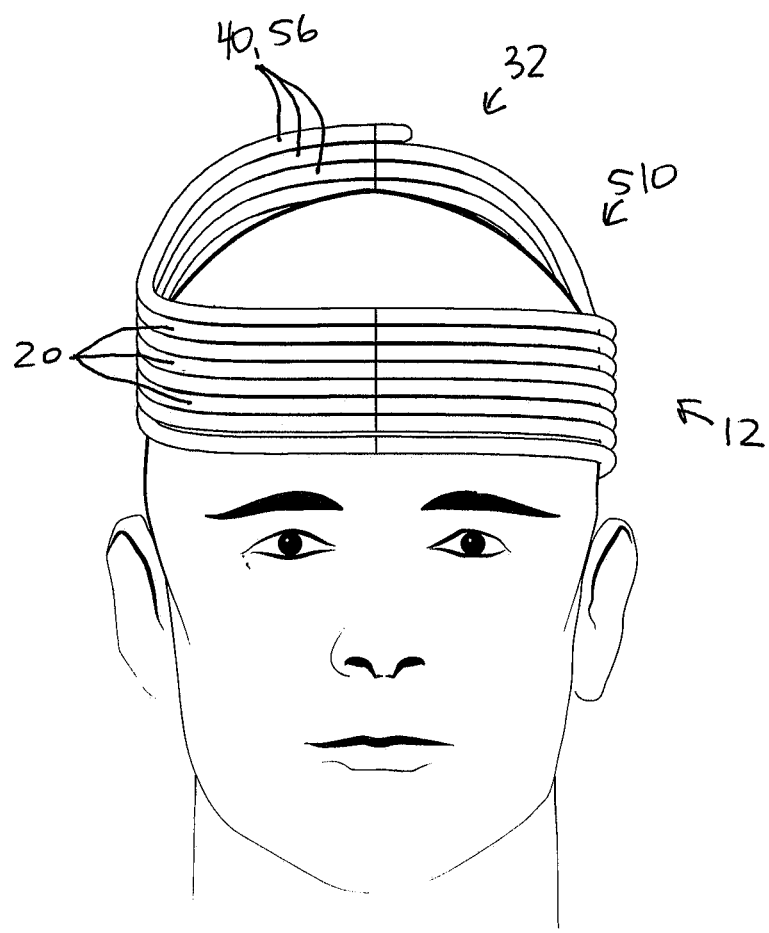
Figure 13D:
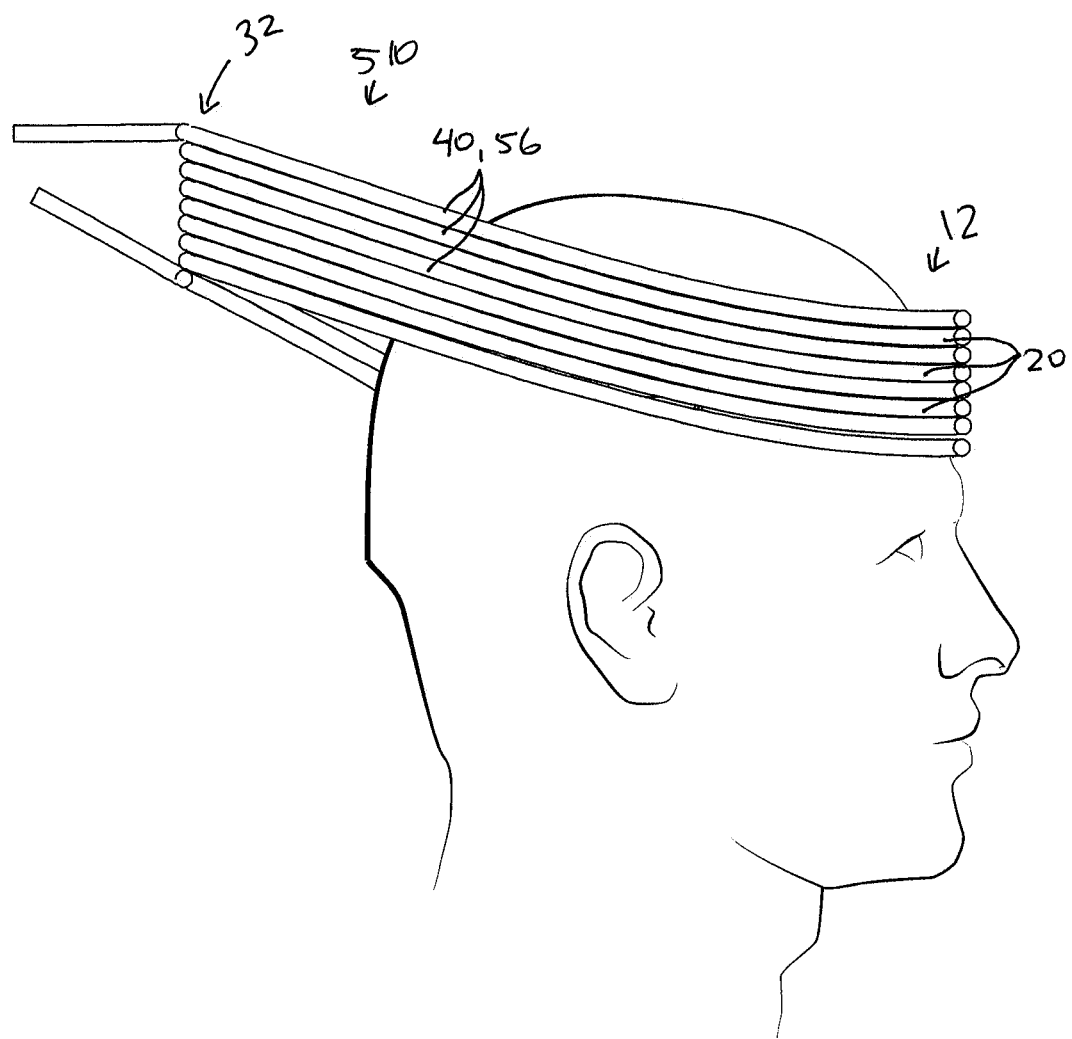

Reference is now made to FIGS. 13A-13D, which are illustrations of a coil 510 in accordance with yet additional embodiments. Coil 510 includes a base portion 12 having multiple stimulating elements 20. Coil 510 further includes a return portion 32 including multiple return elements 40 corresponding to multiple stimulating elements 20. In the embodiment shown herein, base portion 12 is configured to be positioned on frontal section 102 of head 100 and return portion 32 is configured to be positioned protruding from occipital section 108 of head 100. Alternatively, base portion 12 may be positioned on occipital section 108 and return portion may be positioned protruding from frontal section 102 of head 100. Multiple return elements 40 are protruding return elements 56, and extend outwardly from multiple stimulating elements 20 and at an angle thereto. The angle is less than 180 degrees. The angle may be in the horizontal plane, for example, as shown in FIG. 13A. Alternatively, the angle may be in the vertical plane, as shown in FIG. 13B. In some embodiments, return portion 32 may be at a first angle to base portion 12 in the horizontal plane and at a second angle to base portion 12 in the vertical plane. When an angle in the vertical plane is present, when viewed from the front as in FIG. 13C, return elements 40 appear higher than stimulating elements 20. Alternatively, the angle may be in the opposite direction in which case return elements 40 would appear lower than stimulating elements 20. The angle in the vertical plane between stimulating elements 20 and return elements 40 may be a sharp angle, as seen in FIG. 13B as depicted by arrows 150, or may be a gradual slope, as depicted in FIG. 13D. In the embodiment shown in FIG. 13D, return elements 40 are defined as beginning at a point where stimulating elements 20 no longer contact the head. Thus, stimulating elements must have a length of at least 30 cm in order for return elements 40 to be protruding return elements 56.

Coil 410 is used to stimulate brain structures in the orbitofrontal cortex, prefrontal cortex and temporal cortex.

EXAMPLES

The field distribution produced by coil 110 of FIG. 6 was measured in a human head phantom model. A probe was moved in three directions inside the phantom model using a displacement system with 1 mm resolution, and the field distribution of coil 110 was measured in the whole head model volume with 1 cm resolution. Axial and coronal field maps were produced. The field maps were superimposed on anatomical T1-weighted MRI coronal slices, to show the induced field in each anatomical brain region.

Figure 9:
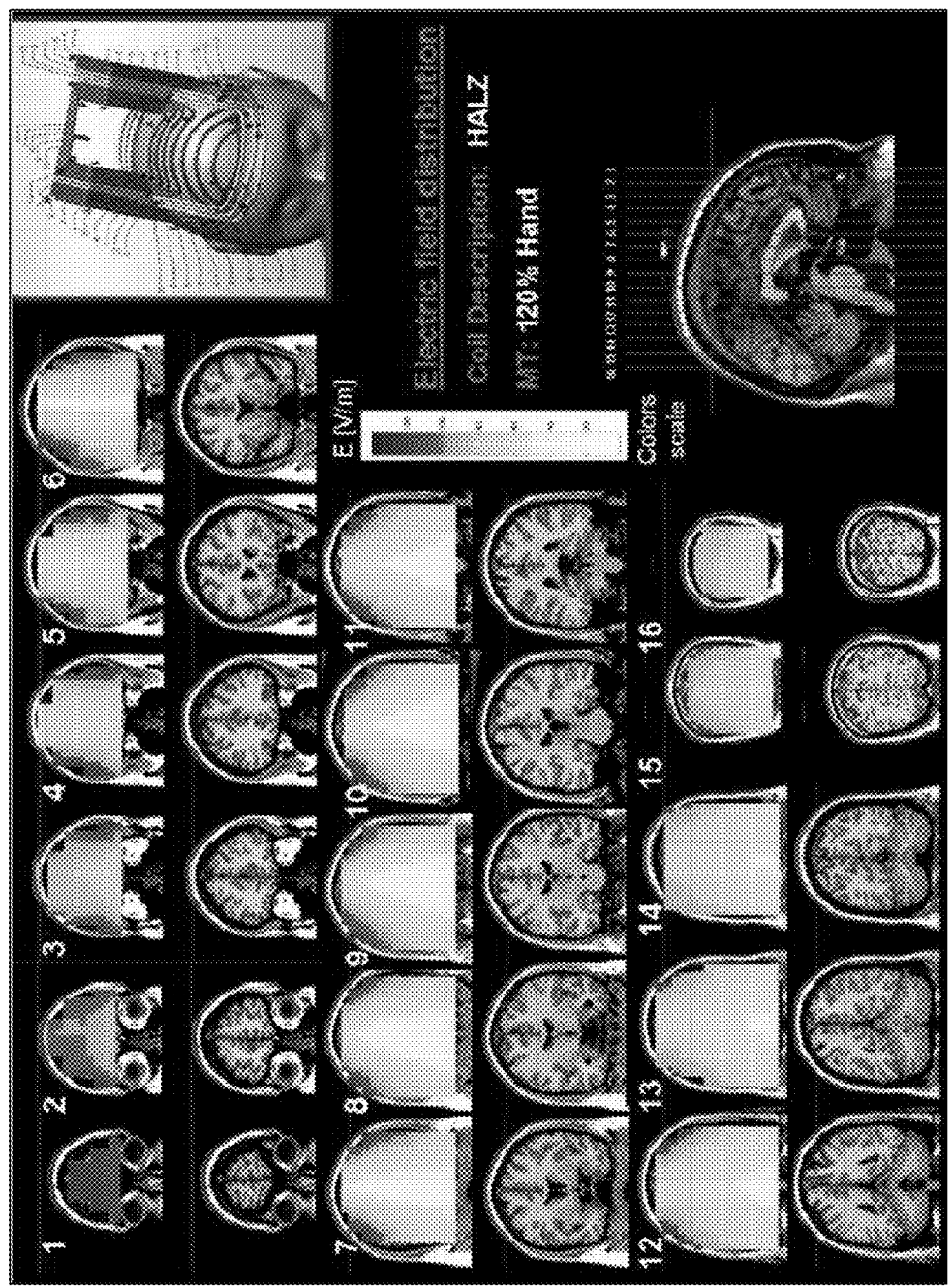
FIG. 9 is an illustration of electric field distribution maps of the coil of FIG. 6, as measured in a human head phantom model.

Reference is now made to FIG. 9, which is an illustration of electric field distribution maps of coil 110 as measured in the human head phantom model. The field maps are shown for stimulator output set at 120% of threshold. The dark pixels indicate field magnitude above the threshold for neuronal activation. The threshold was set to 100 V/m, which is within the accepted range of thresholds required for hand motor activation. The intensity of stimulator power output used for drawing the maps representing the distribution of the electric field for coil 110 was set to the level required to obtain 120% of the neural motor threshold, at a depth of 1.5 cm, according to the approximate depth of hand motor cortex sites. It can be seen that when placing the base portion of coil 110 over the prefrontal cortex, supra-threshold field is induced bilaterally in lateral prefrontal, medial prefrontal and orbitofrontal regions and in parietal regions.

Coil 110 is being used in a clinical trial studying the safety and efficacy of treating subjects suffering from Alzheimer's disease. Subjects receive 3 treatments per week for 4 weeks and 1 treatment/week for an additional 4 weeks. Assessments are performed at 1-8 weeks and also after 16 weeks, i.e. 8 weeks after treatment completion. Analysis after 38 patients revealed that in the group treated with this coil at 10 Hz frequency there was improvement of 0.9 points at the end of the 8 week treatment period and additional improvement of 2.2 points at the 16 week follow up (total improvement of 3.1 points). The sham group showed no change at 8 weeks and a 1.1 point worsening at the 16 week follow up (total worsening of 1.1 points). The percentage of patients improving more than 8 points (responders) in the stimulation group was 18%, as opposed to 7% in the sham group. From the analysis of individual patient data, it appears that those subjects with more severe cognitive dysfunction at baseline may have experienced more improvement from the active treatment than those with less severe cognitive dysfunction at baseline. In the computerized Mindstreams™ global cognitive score, a significant ($p<0.05$) difference was observed in the improvement of the group receiving the treatment, relative to the changes measured in the sham control group in the 8 and 16 weeks time points.

Figure 10:
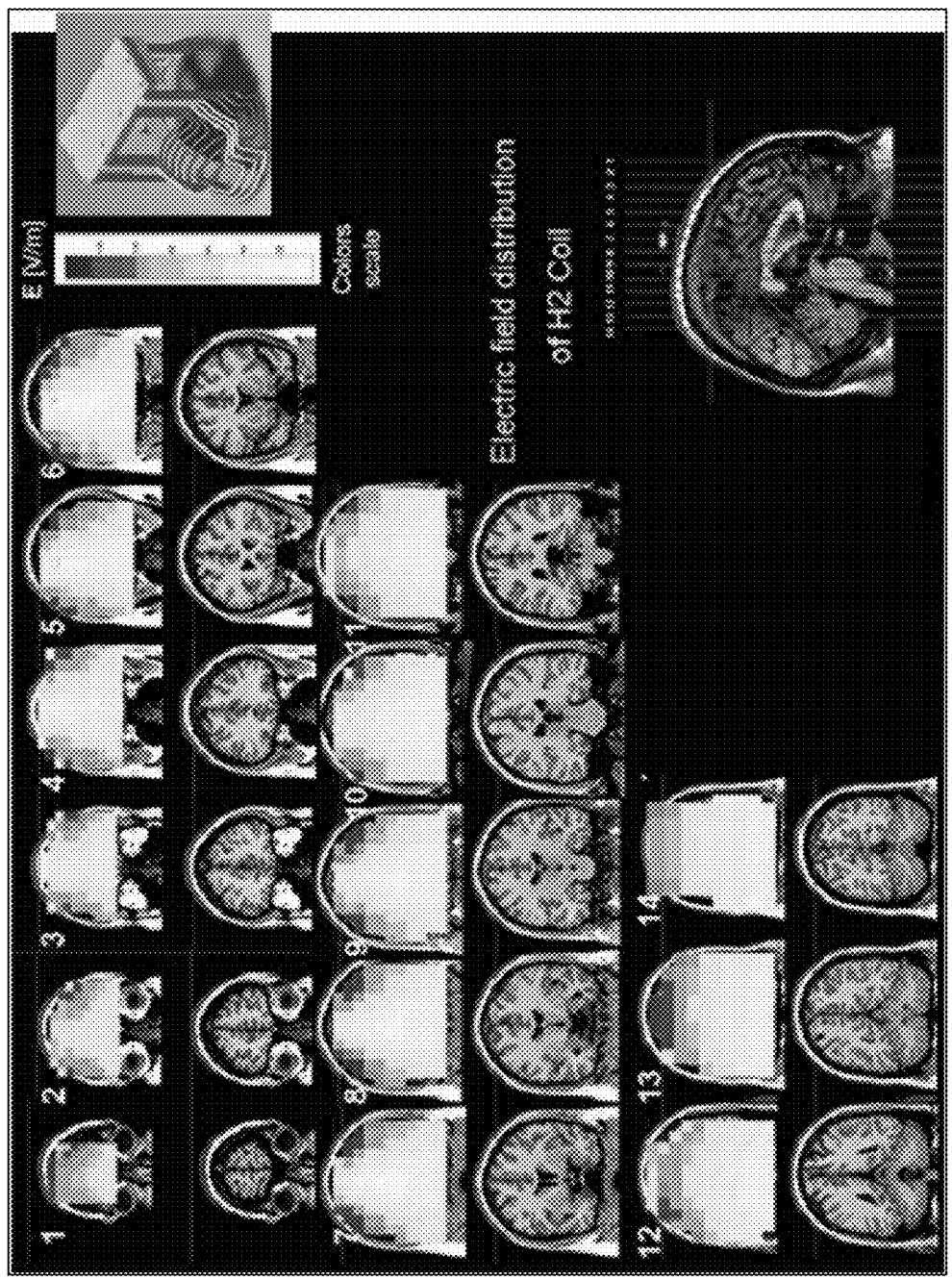
FIG. 10 is an illustration of electric field distribution maps of the coil of FIG. 7 as measured in a human head phantom model.

Reference is now made to FIG. 10, which is an illustration of electric field distribution maps of coil 210 of FIG. 7. The field distribution produced by coil 210 was measured using the same method as for FIG. 9. The field maps are shown for stimulator output set at 120% of motor threshold. It can be seen that when placing the base portion of the coil over the prefrontal cortex, supra-threshold field is induced bilaterally in lateral prefrontal, medial prefrontal and orbitofrontal regions and in parietal regions.

Figure 11:
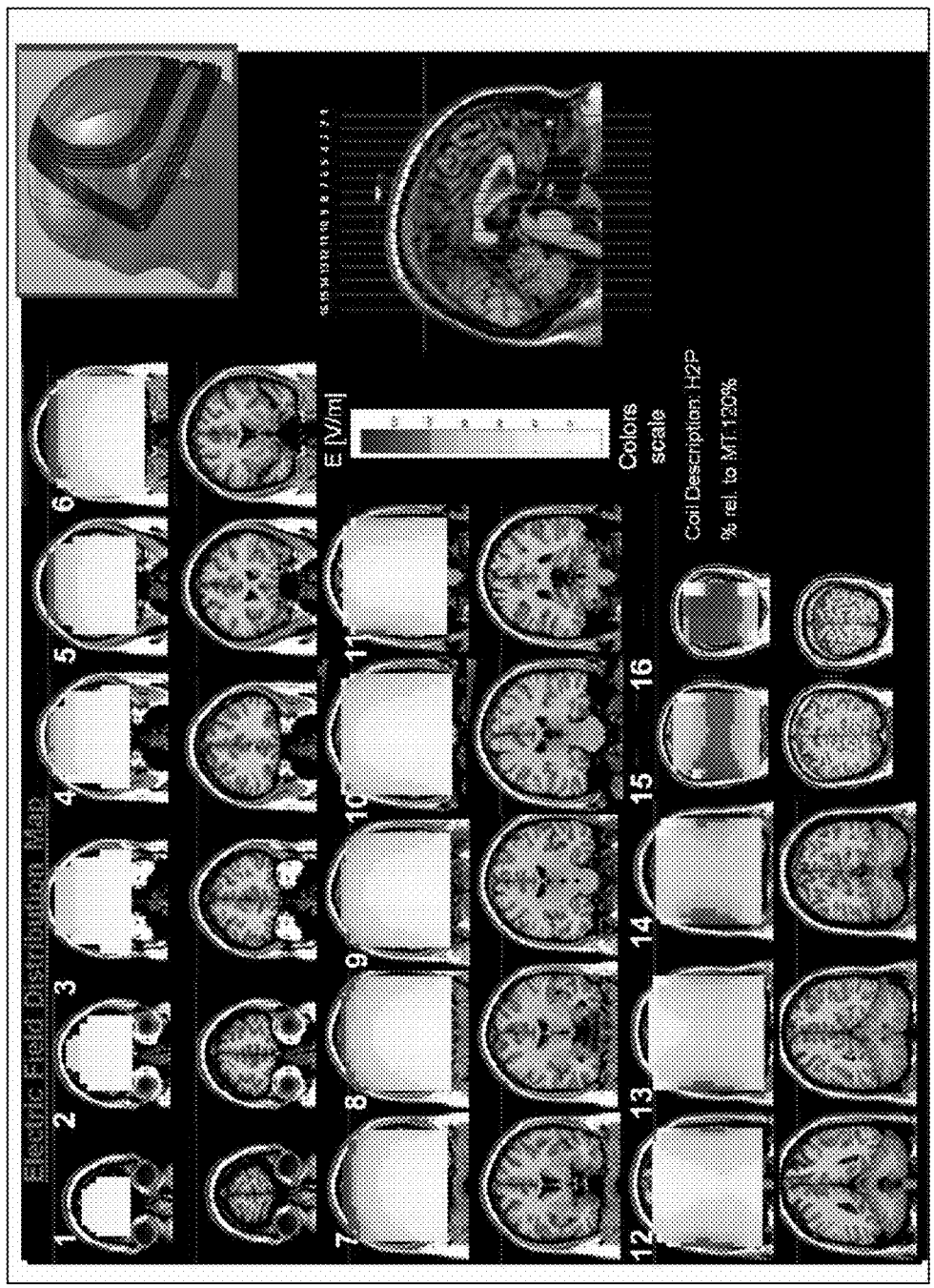
FIG. 11 is an illustration of electric field distribution maps of the coil of FIG. 8 as measured in a human head phantom model.

Reference is now made to FIG. 11, which is an illustration of electric field distribution maps of coil 310 of FIG. 8. The field distribution produced by coil 310 was measured using the same method as for FIG. 9. The field maps are shown for stimulator output set at 120% of motor threshold. It can be seen that when placing the base portion of the coil over the occipital cortex, supra-threshold field is induced bilaterally in occipital and cerebellar regions and in parietal regions.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

While certain features of the present invention have been illustrated and described herein, many modifications, substitutions, changes, and equivalents may occur to those of ordinary skill in the art. It is, therefore, to be understood that the appended claims are intended to cover all such modifications and changes as fall within the true spirit of the present invention.

What is claimed is:

1. A coil for magnetic stimulation of a body part, the coil comprising:
   a base portion including multiple stimulating elements wherein said multiple stimulating elements include a first stimulating element and a second stimulating element adjacent to said first stimulating element, and a third stimulating element adjacent to said second stimulating element, said base portion configured to encircle at least a portion of a first section of a body part and to provide electrical flow in a clockwise or counter-clockwise path; and
   a protruding return portion including multiple protruding return elements wherein each of said multiple protruding return elements is continuous with and positioned at an angle of between 90 and 180 degrees to each of said multiple stimulating elements, wherein said multiple protruding return elements include a first return element and a second return element adjacent to said first return element, and a third return element adjacent to said second return element, said protruding return portion configured to encircle and protrude from, wherein said second section is in a different location than said first section, and to provide electrical flow in a continuation of the clockwise or counter-clockwise path of said base portion, wherein all of said multiple stimulating elements of said base portion are configured to contact the body part and wherein all of said multiple protruding return elements are configured to protrude from the body part, wherein said coil does not include any contacting return elements.

2. The coil of claim 1, wherein said angle is 90 degrees.

3. The coil of claim 1, further comprising multiple first side connecting elements positioned on a first base portion side and multiple second side connecting elements positioned on a second base portion side, said multiple first side connecting elements configured to carry electrical flow from said base portion to said return portion and said multiple second side connecting elements configured to carry electrical flow from said return portion to said base portion wherein all of said connecting elements are configured to contact the body part.

4. The coil of claim 3, wherein said each of said multiple connecting elements has a length of between 10 cm and 30 cm from said base portion to said return portion.

5. The coil of claim 1, wherein said base portion comprises a first base portion group having a first set of multiple stimulating elements separated from one another by a first stimulating distance and a second base portion group positioned below said first base portion group, said second base portion group having a second set of multiple stimulating elements separated from one another by a second stimulating distance, wherein said second base portion group is separated from said first base portion group by a base portion separating distance which is greater than said first stimulating distance and is greater than said second stimulating distance.

6. The coil of claim 1, wherein the body part is a head and wherein said first section and said second section of the body part are at least one of the following: said first section is a frontal section of the head and said second section is a parietal section of the head, said first section is a parietal section of the head and said second section is an occipital section of the head, said first section is a parietal section of the head and said second section is a frontal section of the head and said first section is an occipital section of the head and said second section is a parietal section of the head.

7. The coil of claim 1, wherein the body part is a head and wherein said first section and said section of the body part are at least one of the following: said first section is a frontal section of the head and said second section is an occipital section of the head, or said first section is an occipital section of the head and said second section is a frontal section of the head.

8. The coil of claim 1, wherein said angle is 180 degrees.

9. A coil for magnetic stimulation of a body part, the coil comprising:
   a base portion including multiple stimulating elements wherein said multiple stimulating elements include a first stimulating element and a second stimulating element adjacent to said first stimulating element, and a third stimulating element adjacent to said second stimulating element, said base portion configured to encircle at least a portion of a first section of a body part, said base portion having a first base portion side and a second base portion side and a length from said first base portion side to said second base portion side, said first base portion side configured to be positioned on a first side of said first section of a body part, and second base portion side configured to be positioned on a second side of said first section of a body part, wherein each of the multiple stimulating elements is positioned across the length from said first base portion side to said second base portion side; and
   a protruding return portion including multiple protruding return elements wherein each of said multiple protruding return elements is positioned at an angle of between 90 and 180 degrees to each of said multiple stimulating elements, wherein said multiple protruding return elements include a first return element and a second return element adjacent to said first return element, and a third return element adjacent to said second return element, said protruding return portion configured to encircle and protrude from a second section of the body part, wherein said second section is in a different location than said first section, wherein all of said multiple stimulating elements of said base portion are configured to contact the body part and wherein all of said multiple protruding return elements are configured to protrude from the body part; and wherein said coil does not include any contacting return elements; and
   multiple first side connecting elements positioned on said first base portion side and multiple second side connecting elements positioned on said second base portion side, said multiple first side connecting elements configured to carry electrical flow from said first base portion side to said return portion and said multiple second side connecting elements configured to carry electrical flow from said return portion to said second base portion side wherein all of said connecting elements are configured to contact the body part.

10. The coil of claim 9, wherein said angle is 90 degrees.

11. The coil of claim 9, wherein said angle is 180 degrees.

12. The coil of claim 9, wherein said each of said multiple connecting elements has a length of between 10 cm and 30 cm from said base portion to said return portion.

13. The coil of claim 9, wherein said base portion comprises a first base portion group having a first set of multiple stimulating elements separated from one another by a first stimulating distance and a second base portion group positioned below said first base portion group, said second base portion group having a second set of multiple stimulating elements separated from one another by a second stimulating distance, wherein said second base portion group is separated from said first base portion group by a base portion separating distance which is greater than said first stimulating distance and is greater than said second stimulating distance.

14. The coil of claim 9, wherein the body part is a head and wherein said first section and said second section of the body part are at least one of the following: said first section is a frontal section of the head and said second section is a parietal section of the head, said first section is a parietal section of the head and said second section is an occipital section of the head, said first section is a parietal section of the head and said second section is a frontal section of the head and said first section is an occipital section of the head and said second section is a parietal section of the head.

15. The coil of claim 9, wherein the body part is a head and wherein said first section and said section of the body part are at least one of the following: said first section is a frontal section of the head and said second section is an occipital section of the head, or said first section is an occipital section of the head and said second section is a frontal section of the head.

16. A method of treating a disease, the method comprising: placing a circular coil on a body part, said circular coil including a base portion having parallel adjacent multiple stimulating elements, said base portion configured to encircle at least a portion of a first section of the body part and to provide electrical flow in a circular path, and a protruding return portion having parallel adjacent multiple protruding return elements, wherein each of said multiple protruding return elements is continuous with and positioned at an angle of between 90 and 180 degrees to each of said multiple stimulating elements, said protruding return portion configured to encircle and protrude from at least a portion of a second section of the body part, wherein said second section is in a different location than said first section, and provides electrical flow in a continuation of the circular path of said base portion;

wherein all of said multiple stimulating elements of the circular coil are positioned to be in direct contact with the body part while all of said multiple return elements of the circular coil are positioned to protrude from the body part; and stimulating the body part using said circular coil.

17. The method of claim 16, wherein said treating a disease comprises treating at least one of: depression, bipolar disorder, schizophrenia, Alzheimer's disease, Parkinson's disease, Mild cognitive impairment (MCI), neurodegenerative illnesses, ADHD, drug addiction, cigarette addiction, alcoholism, gambling problem, eating disorders, obesity, autism, Asperger's disease, epilepsy, or migraine.

* * * * *

UNITED STATES PATENT AND TRADEMARK OFFICE
CERTIFICATE OF CORRECTION

PATENT NO. : 9,808,642 B2
APPLICATION NO. : 15/011747
DATED : November 7, 2017
INVENTOR(S) : Abraham Zangen et al.

Page 1 of 1

It is certified that error appears in the above-identified patent and that said Letters Patent is hereby corrected as shown below:

Claim 1, Column 13, Line 22, the text "protrude from" should read -- protrude from a second section of the body part --

Signed and Sealed this
Tenth Day of September, 2019

Andrei Iancu
*Director of the United States Patent and Trademark Office*